(12) United States Patent
Shaw et al.

(10) Patent No.: US 8,331,536 B2
(45) Date of Patent: Dec. 11, 2012

(54) APPARATUS FOR REDUCING SCATTERED X-RAY DETECTION AND METHOD OF SAME

(75) Inventors: Jeffrey Jon Shaw, Ballston Lake, NY (US); Kevin Matthew Durocher, Waterford, NY (US); Kenneth S. Kump, Waukesha, WI (US); Henri Souchay, Versailles (FR)

(73) Assignee: General Electric Company, Niskayuna, NY (US)

( * ) Notice: Subject to any disclaimer, the term of this patent is extended or adjusted under 35 U.S.C. 154(b) by 476 days.

(21) Appl. No.: 12/562,619

(22) Filed: Sep. 18, 2009

(65) Prior Publication Data

US 2011/0069816 A1    Mar. 24, 2011

(51) Int. Cl.
*G21K 1/10* (2006.01)

(52) U.S. Cl. ........................................... 378/154

(58) Field of Classification Search ............. 378/154
See application file for complete search history.

(56) References Cited

U.S. PATENT DOCUMENTS

| | | | |
|---|---|---|---|
| 5,557,650 A | 9/1996 | Guida et al. | |
| 5,991,357 A | 11/1999 | Marcovici et al. | |
| 6,064,720 A | 5/2000 | Piscitelli et al. | |
| 6,181,767 B1 | 1/2001 | Harootian | |
| 7,165,884 B2 | 1/2007 | O'Dea et al. | |
| 7,319,735 B2 | 1/2008 | Defreitas et al. | |
| 7,329,045 B2 | 2/2008 | O'Dea et al. | |
| 7,418,076 B2 | 8/2008 | Li et al. | |
| 7,430,272 B2 | 9/2008 | Jing et al. | |
| 7,443,949 B2 | 10/2008 | Defreitas et al. | |
| 2004/0223590 A1* | 11/2004 | Geiger et al. | 378/154 |
| 2004/0234036 A1* | 11/2004 | Klausz | 378/154 |
| 2004/0251420 A1 | 12/2004 | Sun | |
| 2005/0111617 A1* | 5/2005 | Shoji | 378/37 |
| 2006/0023832 A1 | 2/2006 | Edic et al. | |
| 2008/0165931 A1 | 7/2008 | Luusua | |

FOREIGN PATENT DOCUMENTS

| | | |
|---|---|---|
| EP | 1943950 A1 | 7/2008 |
| WO | 2007061152 A1 | 5/2007 |

* cited by examiner

*Primary Examiner* — Glen Kao
(74) *Attorney, Agent, or Firm* — Scott J. Asmus

(57) ABSTRACT

A method, system, and apparatus including an x-ray detector unit that includes an anti-scatter grid free of at least one of a top cover and a bottom cover, a flat panel x-ray detector having an x-ray conversion layer, and an integrated anti-scatter grid assembly configured to provide structural support to the anti-scatter grid and to provide mechanical protection to the flat panel x-ray detector. The anti-scatter grid is configured to absorb a plurality of scattered x-rays impinging on the anti-scatter grid while substantially allowing un-scattered x-rays to pass through the anti-scatter grid. The x-ray conversion layer is configured to convert an x-ray into visible light or an electronic signal. The flat panel x-ray detector is fixed relative to the anti-scatter grid such that the anti-scatter grid remains stationary relative to the flat panel x-ray detector during operation of the x-ray detector.

16 Claims, 4 Drawing Sheets

APPARATUS FOR REDUCING SCATTERED X-RAY DETECTION AND METHOD OF SAME

BACKGROUND OF THE INVENTION

The invention relates generally to x-ray detectors and, more particularly, to an apparatus and method of reducing scattered x-ray detection in an x-ray detector.

X-ray imaging is a non-invasive technique to capture images of medical patients for clinical diagnosis as well as inspect the contents of sealed containers, such as luggage, packages, and other parcels. To capture these images, an x-ray source irradiates a scan subject (or object) with a fan beam of x-rays. The x-rays are then attenuated as they pass through the scan subject. The degree of attenuation varies across the scan subject as a result of variances in the internal composition of the subject. The attenuated energy impinges upon an x-ray detector designed to convert the attenuating energy to a form usable in image reconstruction. A control system reads out electrical charge stored in the x-ray detector and generates a corresponding image. For a conventional, screen film detector, the image is developed on a film and displayed using a backlight.

Presently, flat panel, digital x-ray detectors are being used to acquire data for image reconstruction. Flat panel detectors are generally constructed as having a scintillator, which is used to convert x-rays to visible light that can be detected by a photosensitive layer. The photosensitive layer includes an array of photosensitive or detection elements, where each element stores electrical charge in proportion to the light that is individually detected. Generally, each detection element has a light sensitive region and a region of electronics to control the storage and output of electrical charge. The light sensitive region typically includes a photoconductor, and electrons are released in the photoconductor when exposed to visible light. During this exposure, charge is collected in each detector element and is stored in a capacitor situated in the electronics region. After exposure, the charge in each detector element is read out using logic controlled electronics.

Each detector element may be controlled using a transistor-based switch. In this regard, the source of the transistor is connected to the capacitor, the drain of the transistor is connected to a readout line, and the gate of the transistor is connected to a scan control interface disposed on the electronics in the detector. When negative voltage is applied to the gate, the switch is driven to an OFF state, i.e., no conduction between the source and drain. On the other hand, when a positive voltage is applied to the gate, the switch is turned ON resulting in connection of the source to the drain. Often, each detector element of the detector array is constructed with a respective transistor and is controlled in a manner consistent with that described below.

For example, during exposure to x-rays, negative voltage is applied to all gate lines resulting in all the transistor switches being driven to or placed in an OFF state. As a result, any charge accumulated during exposure is stored in each detector element capacitor. During read out, positive voltage is sequentially applied to each gate line, one gate at a time. In this regard, generally only one detector element is read out at a time. A multiplexer may also be used to support readout of the detector elements in a raster fashion. An advantage of sequentially reading out each detector element individually is that the charge from one detector element does not pass through any other detector elements. The output of each detector element is then input to a digitizer that digitizes the acquired signals for subsequent image reconstruction on a per pixel basis. Each pixel of the reconstructed image corresponds to a single detector element of the detector array.

As described above, digital x-ray detectors utilize a layer of scintillating material, such as Cesium iodide (CsI), to convert incident radiation to visible light that is detected by light sensitive regions of individual detector elements of a detector array. Generally, transistor controlled detector elements are supported on a thin substrate of glass. The substrate, which supports the detector elements as well as the scintillator layer, is supported by a panel support. The panel support is not only designed to support the detector components, but also isolates the electronics that control the detector from the image detecting components. The electronics are supported by the panel support and enclosed by the back cover.

Many x-ray systems employ an anti-scatter grid. A primary function of the anti-scatter grid is to preferentially pass primary x-rays and reject scattered x-rays (e.g., Compton scattered x-rays). Accordingly, unwanted x-ray scatter is generally reduced when an anti-scatter grid is employed.

Scattered x-rays are objectionable because they often cause noise (e.g., image artifacts) to be present in a resulting x-ray image. Absent an anti-scatter grid, an x-ray image is often degraded by x-rays that are Compton scattered through the patient or object. Such scattered x-rays generally blur resulting images. As such, clinicians such as radiologists may have a difficult time interpreting such degraded images.

Typically, an anti-scatter grid is freestanding and is moveable relative to an x-ray detector. Such an anti-scatter grid is placed outside an x-ray detector. Often, such grids are packaged in a "cassette" located just beneath a patient support plate or Bucky cover. The cassettes generally require grid covers that provide mechanical support. These grid covers along with the Bucky cover, however, are known to absorb x-rays. Since these covers absorb x-rays, it is often necessary to increase the x-ray dosage to obtain desired image properties.

An anti-scatter grid typically includes a plurality of thin strips of a highly x-ray absorbing material, such as lead, that are placed parallel to one another along an edge. Rather than overlapping, however, the strips, generally referred to as septa, are typically arranged such that a uniform gap appears between edges of adjacent septa. Further, the septa are angled relative to one another such that the anti-scatter grid is substantially focused toward the x-ray source. As such, non-scattered x-rays from the x-ray source are more likely to pass through the gaps of the anti-scatter grid, and scattered x-rays are more likely to be absorbed by the anti-scatter grid. Accordingly, such anti-scatter grids are designed, in theory, to allow primary x-rays to pass therethrough while absorbing scattered x-rays. Unfortunately, in practice, such anti-scatter grids also absorb some primary x-rays. Typically, there is a tradeoff between good scatter rejection (absorption) and high primary x-ray transmission. This tradeoff is often captured in the quantum improvement factor (QIF). Typically, QIF Values above 1 indicate better imaging while those below 1 indicate that the anti-scatter grid may be degrading image quality. A typical mammographic anti-scatter grid might have a QIF value of about 1.05 to 1.1.

For x-ray detectors having a very fine pixel structure, such as detectors employed in mammography, the grid septa pattern may interfere with the pixel pattern on the detector. Such interference often manifests itself as interference lines, commonly called Moire patterning, in the resulting x-ray image. In such cases, the anti-scatter grid is moved relative to the x-ray detector during x-ray exposure to eliminate the patterning. Unfortunately, increased costs and complexities are generally associated with anti-scatter grids having moving capabilities.

Advanced three-dimensional (3D) mammography systems employing tomography have been developed and are entering the marketplace. In tomography, an x-ray tube is moved through an arc, acquiring many x-ray images over the course of travel. These images may be combined to build up a 3D image aiding cancer diagnosis. There is not, however, a generally accepted practical method or practice for employing the use of conventional anti-scatter grids in 3D tomography-type mammography systems.

Therefore, it would be desirable to design an apparatus and method that overcomes the aforementioned drawbacks.

BRIEF DESCRIPTION OF THE INVENTION

The invention is directed to a method and apparatus for x-ray imaging systems and, more particularly, to x-ray detectors having an anti-scatter grid incorporated therein.

In accordance with one aspect of the invention, an x-ray detector unit includes an anti-scatter grid free of at least one of a top cover and a bottom cover, a flat panel x-ray detector having an x-ray conversion layer, and an integrated anti-scatter grid assembly configured to provide structural support to the anti-scatter grid and to provide mechanical protection to the flat panel x-ray detector. The anti-scatter grid is configured to absorb a plurality of scattered x-rays impinging on the anti-scatter grid while substantially allowing un-scattered x-rays to pass through the anti-scatter grid. The x-ray conversion layer is configured to convert an x-ray into visible light or an electronic signal. The flat panel x-ray detector is fixed relative to the anti-scatter grid such that the anti-scatter grid remains stationary relative to the flat panel x-ray detector during operation of the x-ray detector.

According to another aspect of the invention, a method of manufacturing an x-ray detector unit includes forming an integrated anti-scatter grid assembly removably coupleable to an x-ray imaging system, coupling a flat panel x-ray detector to the integrated anti-scatter grid assembly, forming an anti-scatter grid having top portion and a bottom portion, and coupling the anti-scatter grid to the integrated anti-scatter grid assembly. The integrated anti-scatter grid assembly is configured to support an imaging object and the anti-scatter grid is configured to absorb at least a portion of a plurality of scattered x-rays while allowing a plurality of non-scattered x-rays to pass therethrough. The anti-scatter grid is also configured to remain stationary relative to the flat panel x-ray detector during operation of the flat panel x-ray detector.

In accordance with yet another aspect of the invention, an x-ray detector unit includes an integrated anti-scatter grid assembly, a flat panel x-ray detector coupled to the integrated anti-scatter grid assembly, and an anti-scatter grid coupled to the integrated anti-scatter grid assembly such that the anti-scatter grid remains in a substantially fixed position in relation to the flat panel x-ray detector during operation of the flat panel x-ray detector. The anti-scatter grid includes a plurality of septa having a length dimension greater than a width dimension and arranged such that the length dimension of each septum of the plurality of septa is substantially parallel to a length dimension of an adjacent septum of the plurality of septa. The anti-scatter grid is configured to allow x-rays to pass between adjacent septa of the plurality of septa. The integrated anti-scatter grid assembly is configured to support an imaging object and is configured to provide mechanical protection to the flat panel x-ray detector. The flat panel x-ray detector is configured to transmit information indicative of attenuated x-rays to a processor.

Various other features and advantages will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Embodiments of the invention may be employed with a variety of two-dimensional and three-dimensional x-ray imaging systems.

Figure 1:
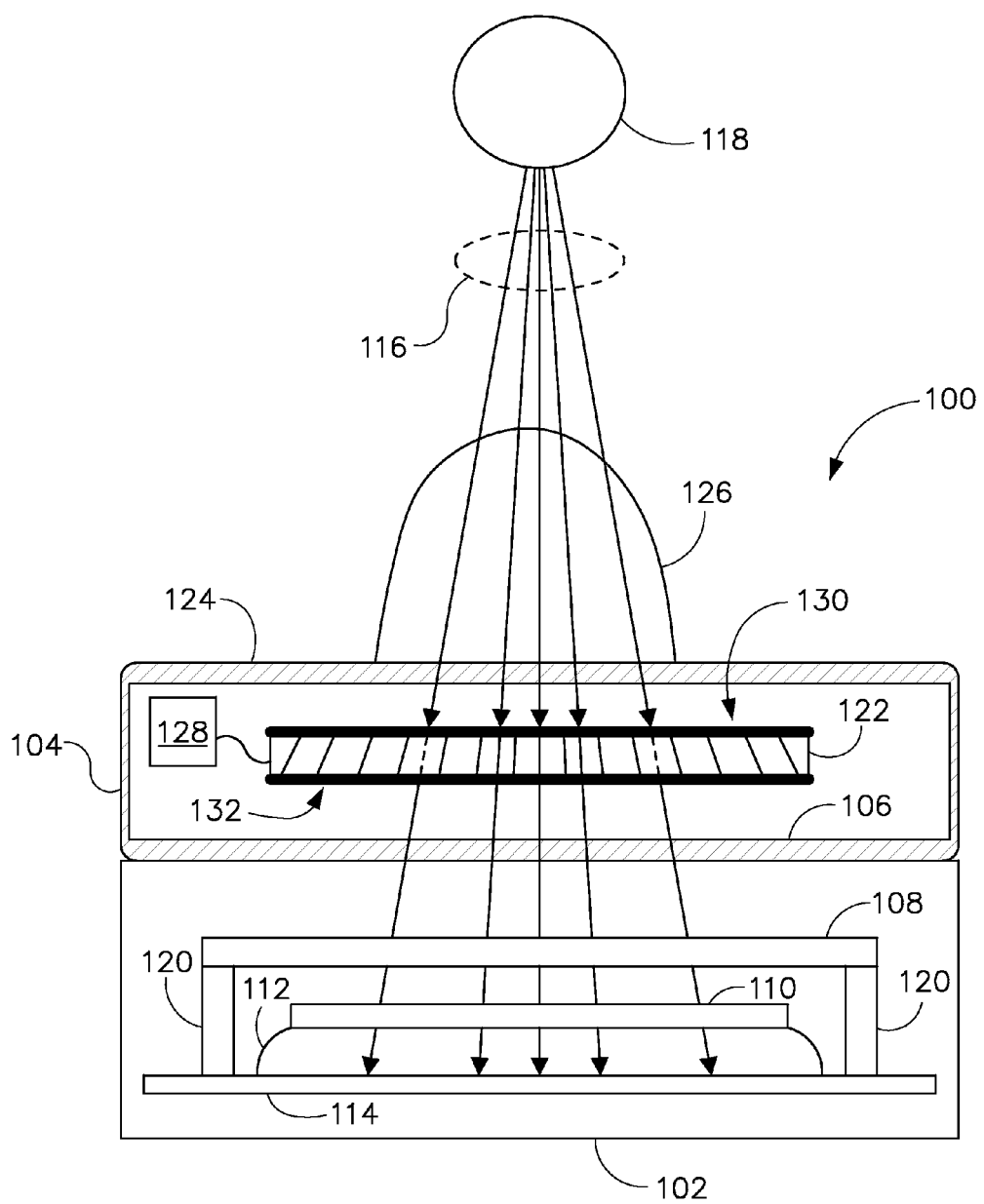
FIG. 1 is a schematic representation of x-ray system modules of exemplary prior art.

Referring to FIG. 1, a plurality of x-ray system modules 100 are shown according to exemplary prior art. As shown in FIG. 1, x-ray system modules 100 include a flat panel x-ray detector 102 and an anti-scatter grid system 104. Flat panel x-ray detector 102 includes a detector cover 106, an x-ray panel cover 108, a reflective film 110, an x-ray conversion component 112, and an x-ray panel 114. X-ray conversion component 112 may, for example, comprise a scintillator that converts x-ray energy from a plurality of x-rays 116 from an x-ray source 118 to visible light that is subsequently detected by a photodiode array (not shown) on x-ray panel 114 that converts the visible light to an electric signal. Alternatively, x-ray conversion component 100 may comprise a direct conversion material such as amorphous selenium, which directly converts x-ray energy to an electric signal. In such an instance (i.e., when utilizing a direct conversion material), reflective film 110 may not be needed. A coupling material 120, such as an epoxy, couples x-ray panel cover 108 to x-ray panel 114.

Flat panel x-ray detector 102 is mounted or coupled to anti-scatter grid system 104. Anti-scatter grid system 104 includes an anti-scatter grid 122, also known as a Bucky. Anti-scatter grid 104 is protected by a cover panel 124, often referred to as a Bucky cover, which provides support for a patient/object object 126 or a portion thereof and provides structural support for anti-scatter grid system 104.

Anti-scatter grid 122 is configured to be a freestanding component that is moveable relative to flat panel x-ray detector 102 to avoid or at least minimize patterning such as Moire patterns or the like that result from the alignment of anti-scatter grid 122 to flat panel x-ray detector 102. That is, anti-scatter grid 122 is configured to move, typically by a servo 128, as plurality of x-rays 116 pass therethrough to conversion component 112. Accordingly, patterning, such as Moire patterning, is reduced in resulting images.

As discussed above, cover panel 124 of anti-scatter grid 104 provides mechanical or structural support for anti-scatter grid system 104 and also provides support for object 126 being imaged. However, cover panel 124 also absorbs impinging x-rays. Accordingly, plurality of x-rays 116 are attenuated as they pass through cover panel 124. X-ray dosage, therefore, typically often needs to be increased to take into account the x-ray absorption by cover panel 124. Therefore, object 126 is subject to a greater x-ray dosage.

Coupled to anti-scatter grid 122 is a top cover 130 and a bottom cover 132 that provide structural support for anti-scatter grid 122. Similar to cover panel 124, top and bottom covers 130, 132, respectively, also attenuate plurality of x-rays 116 as they pass therethrough. This type of attenuation can also lead to the need to increase the x-ray dosage object 126 is exposed to.

Similarly, detector cover 106 and x-ray panel cover 108 also attenuate plurality of x-rays 116 passing therethrough. As such, the x-ray dosage object 126 is exposed to is calibrated (i.e., x-ray dosage is increased) to take into account such attenuation.

Figure 2:
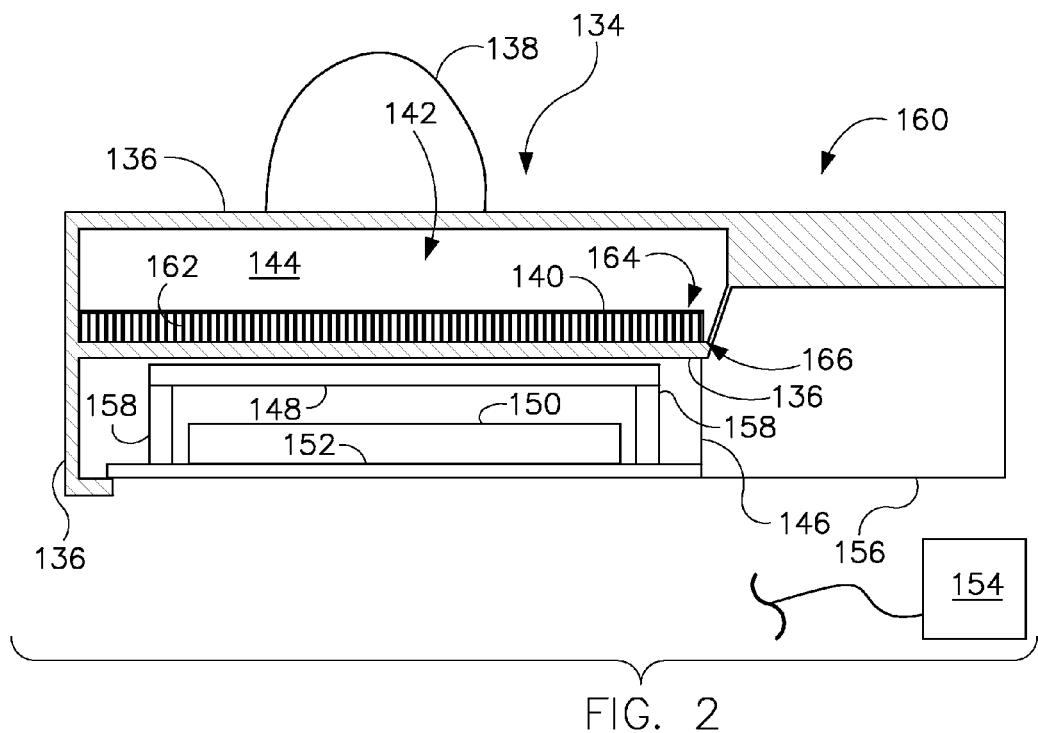
FIG. 2 is a block schematic diagram of a cross-sectional view of an x-ray detector unit according to an embodiment of the invention.

Referring now to FIG. 2, an x-ray detector unit or assembly 134 is shown in a schematic cross-sectional perspective according to an embodiment of the invention. X-ray detector unit 134 includes a support structure or integrated anti-scatter grid assembly 136 capable of supporting an imaging object 138 and an anti-scatter grid 140 within a portion or pocket 142 of integrated anti-scatter grid assembly 136. It is contemplated that integrated anti-scatter grid assembly 136 may comprise a carbon composite or other relatively x-ray transparent material.

Anti-scatter grid 140 is integrated into pocket 142 of integrated anti-scatter grid assembly 136. Further, a foam-like material 144 is positioned in pocket 142 to provide support to anti-scatter grid 140. As shown, it is contemplated that anti-scatter grid 140 may be free of top and bottom anti-scatter grid covers. However, it is also contemplated that anti-scatter grid 140 may include a top and/or bottom grid cover (not shown) to provide additional support.

In addition to anti-scatter grid 140 and integrated anti-scatter grid assembly 136, x-ray detector unit 134 also includes a flat panel x-ray detector 146 coupled to integrated anti-scatter grid assembly 136. Integrated anti-scatter grid assembly 136 provides structural support to anti-scatter grid 140 and also provides mechanical protection to flat panel x-ray detector 146.

Flat panel x-ray detector 146 includes a panel cover 148, an x-ray conversion component 150, an x-ray panel 152 that transmits attenuated x-ray data to a processor 154, and a set of electronics 156 for controlling flat panel x-ray detector 146. A coupling material 158 such as an epoxy couples panel cover 148 to x-ray panel 152. Conversion component 150 may, for example, comprise a scintillator material or a direct conversion material such as amorphous selenium.

As shown in FIG. 2, flat panel x-ray detector 146 is coupled to the underside of integrated anti-scatter grid assembly 136. It is contemplated, as shown in FIG. 2, that a portion 160 of the material that makes up integrated anti-scatter grid assembly 136 may be a thickness greater than other portions of integrated anti-scatter grid assembly 136. As depicted, portion 160 lies above electronics 156, but not over conversion material 150. As such, portion 160 of integrated anti-scatter grid assembly 136 can provide further structural support to x-ray detector unit assembly 134 without unnecessarily adding more material over conversion material 150 that could absorb un-scattered x-rays.

Anti-scatter grid 140 of x-ray detector unit 134 includes a plurality of "lines" or septa 162 and is configured to block scattered x-rays (not shown) via plurality of septa 162, while allowing primary (i.e., un-scattered x-rays) to pass between plurality of septa 162. It is contemplated that the gaps between consecutive septa of plurality of septa 162 be filled with a material transparent or substantially transparent to x-rays, such as graphite, carbon composite, or aluminum.

According to the present embodiment, anti-scatter grid 140 need not include a top cover such as top cover 130 of FIG. 1. Rather, foam-like material 144 of FIG. 2, which is more x-ray transparent per cubic inch than integrated anti-scatter grid assembly 136, provides structural support to a top portion 164 of anti-scatter grid 140. Foam-like material 144 may comprise a variety of materials such as a rigid polymethacrylimide (i.e., PMI foam).

Anti-scatter grid 140 also need not include a bottom cover such as bottom cover 132 of FIG. 1. Rather, integrated anti-scatter grid assembly 136 of FIG. 2 is coupled to a bottom portion 166 of anti-scatter grid 140 and provides structural support to anti-scatter grid 140. It is also noted that a Bucky cover such as cover panel 124 of FIG. 1 is not associated with anti-scatter grid 140 of FIG. 2. Further details regarding anti-scatter grid 140 will be set forth in greater detail below with respect to FIG. 4

Anti-scatter grid 140 and flat panel detector 146 are coupled to support structure or integrated anti-scatter grid assembly 136 in such a manner that keeps anti-scatter grid 140 stationary relative to flat panel detector 146 during operation of flat panel detector 146 (i.e., during imaging). Patterning, such as Moire patterning, is avoided or at least minimized by ensuring that anti-scatter grid 140 is configured to have a line frequency (e.g., the number of septa 162 per inch) greater than two-hundred lines per inch.

In comparison to the exemplary prior art depicted in FIG. 1, x-ray detector unit 134 of FIG. 2 avoids the need to employ a Bucky cover such as cover panel 124 of FIG. 1 and also avoids the need to employ anti-scatter grid top and bottom panels (e.g., top and bottom covers 130, 132 respectively of FIG. 1). Accordingly, the x-ray dosage to object 138 can be reduced since x-rays do not have to pass through these additional layers. Integrated anti-scatter grid assembly 136 effectively serves as a detector cover for flat panel detector 146 and a support for anti-scatter grid 140 while also providing structural support to x-ray detector unit 134 as a whole.

Figure 3:
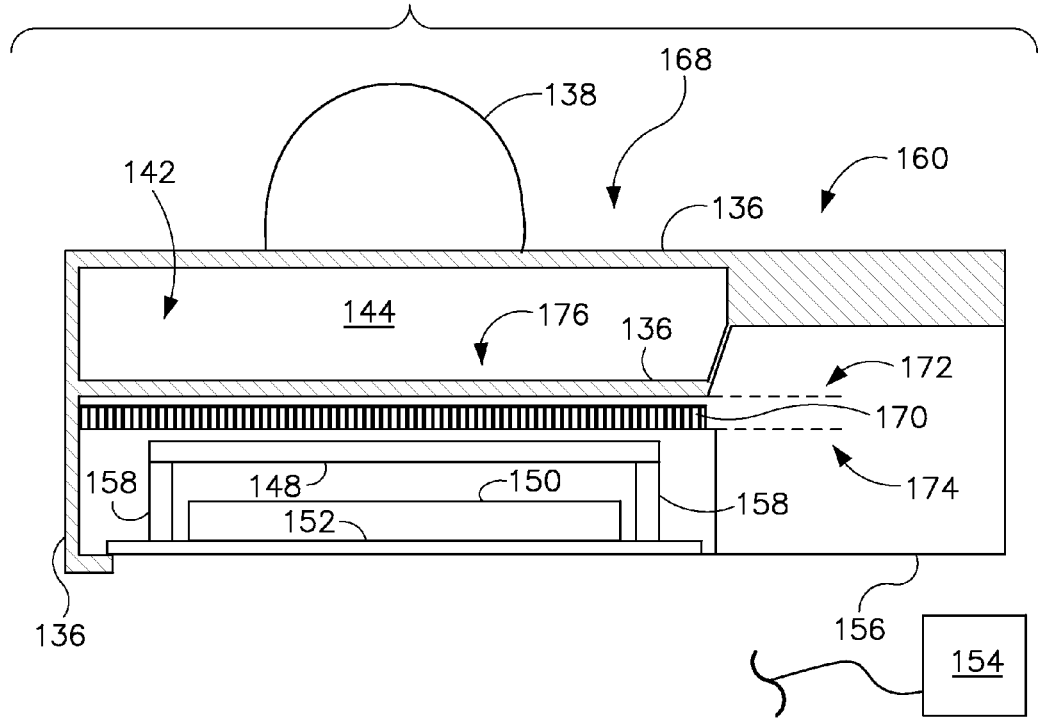
FIG. 3 is a block schematic diagram of a cross-sectional view of an x-ray detector unit according to another embodiment of the invention.

Referring now to FIG. 3, an x-ray detector unit or assembly 168 is illustrated in a cross-sectional view according to another embodiment of the invention. Components similar to those components shown in FIG. 2 are shown with like reference numerals. Similar to anti-scatter grid 140 of FIG. 2, x-ray detector unit 168 includes an anti-scatter grid 170 having a top portion 172 and a bottom portion 174 free of an anti-scatter grid top and bottom cover, respectively. However, in contrast to the embodiment represented in FIG. 2, anti-scatter grid 170 of FIG. 3 is not positioned within pocket 142 of integrated anti-scatter grid assembly 136. Rather, top portion 172 of anti-scatter grid 170 is coupled to a portion 176 of integrated anti-scatter grid assembly 136 outside of pocket 142. As such, in the present embodiment, integrated anti-scatter grid assembly 136 provides structural support and/or rigidity to anti-scatter grid 170 while also providing mechanical protection to flat panel x-ray detector 146. Flat panel x-ray detector 146, being coupled to bottom portion 174 of anti-scatter grid 170, also provides structural support and/or rigidity to anti-scatter grid 170. Though in the present embodiment anti-scatter grid 170 is free of a top cover (not shown) and a bottom cover (not shown), it is contemplated that anti-scatter grid 170 may include a top and/or bottom cover (not shown) to provide further structural support.

Similar to the embodiment represented in FIG. 2, anti-scatter grid 170 of FIG. 3 and flat panel detector 146 are coupled to integrated anti-scatter grid assembly 136 in such a manner that anti-scatter grid 170 remains in a substantially fixed position relative to flat panel detector 146 during imaging. Patterning is avoided or at least minimized in resulting images by ensuring that anti-scatter grid 170 has a line frequency or density greater than two-hundred lines per inch.

In comparison to the exemplary prior art depicted in FIG. 1, x-ray detector unit 168 of FIG. 3 avoids the need to employ a Bucky cover, such as cover panel 124 of FIG. 1 and also avoids the need to employ anti-scatter grid top and bottom panels (e.g., top and bottom covers 130, 132 respectively of FIG. 1). Accordingly, the x-ray dosage to object 138 can be reduced.

Figure 4:
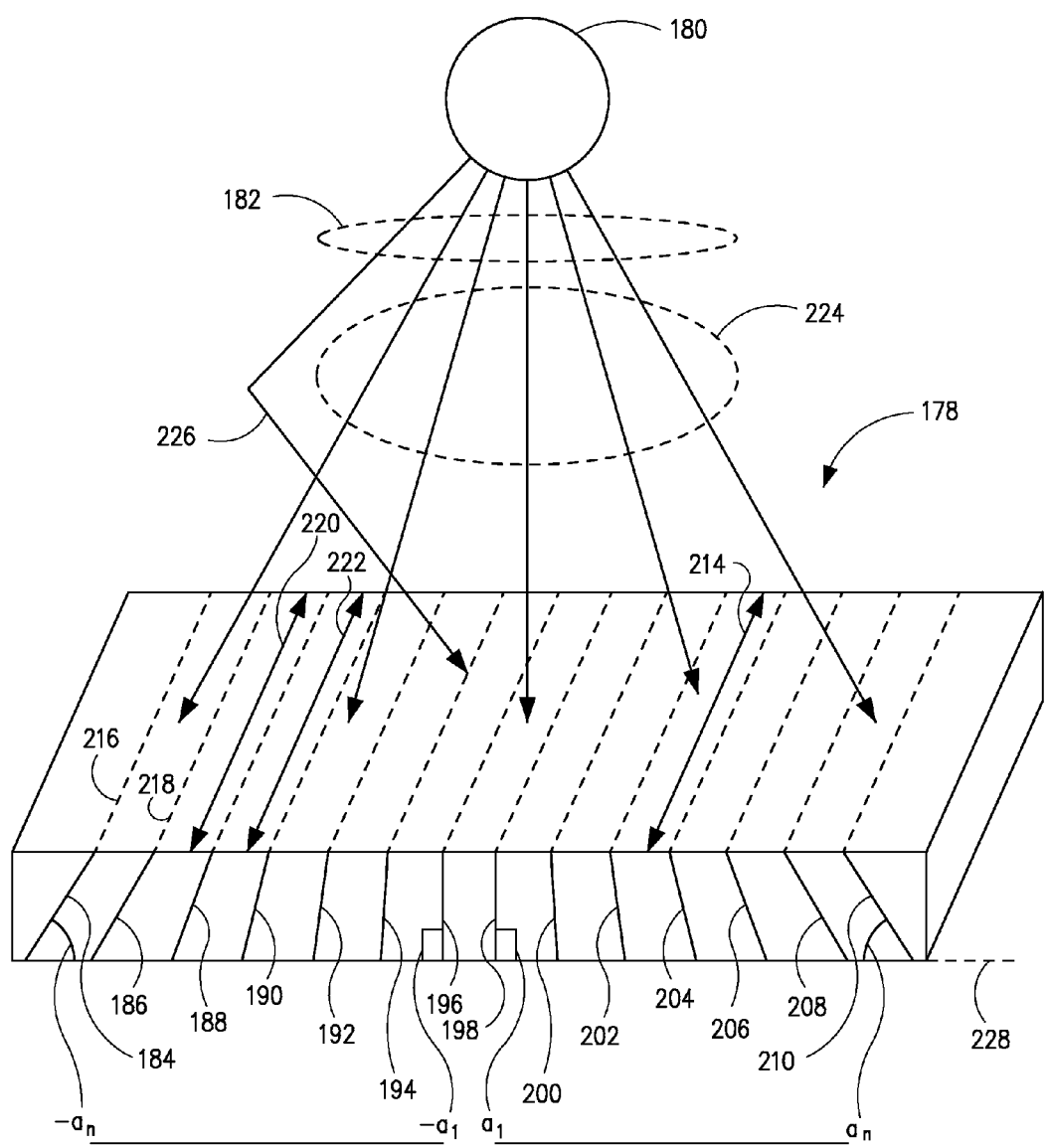
FIG. 4 is a block schematic diagram of a schematic view of an anti-scatter grid according to another embodiment of the invention.

Referring now to FIG. 4, a schematic view of an anti-scatter grid 178 is shown according to an embodiment of the invention. In addition to anti-scatter grid 178, FIG. 4 depicts an x-ray source 180 emitting a plurality of x-rays 182 that are impinging onto anti-scatter grid 178.

Anti-scatter grid 178 includes a plurality of septa 184-210, each having a width dimension 212 and a length dimension 214. Septa 184-210 may comprise a variety of substances (e.g., lead). An edge of each septum 184-210 runs parallel to an edge of an adjacent septum. For example, an edge 216 of septum 184 runs parallel to an edge 218 of septum 186. In other words, a length dimension 220 of septum 188 runs parallel to a length dimension 222 of septum 190.

Septa 184 are arranged or oriented to allow un-scattered x-rays to pass through anti-scatter grid 178 while blocking (e.g., absorbing) scattered x-rays that proceed to anti-scatter grid 178. For example, a plurality of x-rays 224 that pass from x-ray source 180 through an imaging or other object (not shown) and remain un-scattered by the object, pass between septa 184-210 and through anti-scatter grid 178. However, a scattered x-ray is likely to be blocked or absorbed by one of septa 184-210. For example, as shown in FIG. 4, a scattered x-ray 226 is blocked or absorbed by septum 194. By blocking scattered x-rays, resulting images are less prone to artifacts.

In the present embodiment, the orientations of septa 184-210 relative to a reference line 228 are manipulated so that scattered x-rays (e.g., scattered x-ray 226) are blocked by anti-scatter grid 178. For example, the angles $-\alpha_n$ to $-\alpha_1$ between respective septa 184-196 and reference line 228 decrease from $-\alpha_1$ to $-\alpha_n$. Similarly, the angles $\alpha_1$ to $\alpha_n$ between respective septa 198-210 and reference line 228 decrease from $\alpha_1$ to $\alpha_n$. Such an arrangement blocks much of the scattered x-rays while allowing much of the un-scattered x-rays to pass therethrough.

Anti-scatter grid 178 represents and exemplary embodiment. Anti-scatter grids having other configurations are contemplated.

Figure 5:
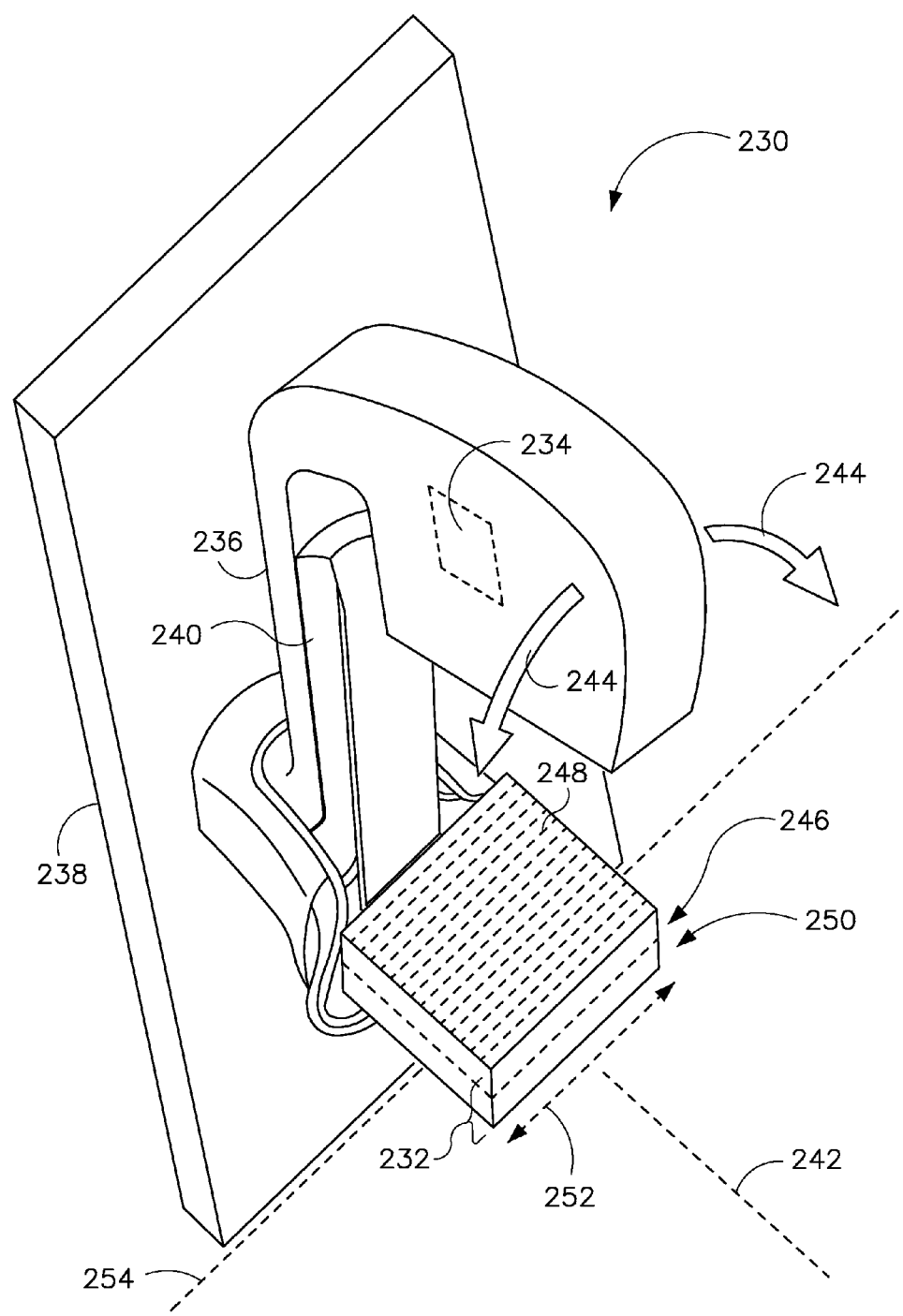
FIG. 5 is a schematic representation of a mammography x-ray 3D imaging system.

Referring now to FIG. 5, a schematic representation of mammography x-ray 3D imaging system 230 having an x-ray detector unit 232 coupled thereto is shown according to an embodiment of the invention. Mammography x-ray imaging system 230 includes an x-ray tube 234 attached to a first arm 236, which first arm 236 is pivotally attached to a support 238. X-ray detector unit 232 is attached to a second arm 240. X-ray source or tube 234 is moveable about an axis of rotation 242 such that x-ray tube 234 is movable along an arcuate path 244.

As shown in a FIG. 5, x-ray detector unit 232 includes an anti-scatter grid 246 having a plurality of septa 248 and a flat panel x-ray detector 250. Similar to embodiments represented in FIGS. 2 and 3, septa 248 remain substantially stationary relative to flat panel detector 250 during imaging.

Relative to x-ray tube 234, x-ray detector unit 232 is positioned such that a length dimension 252 of each septum 248 is substantially perpendicular to axis of rotation 242. In other words, a projection 254 of arcuate path 244 onto x-ray detector unit 232 runs substantially parallel to the edges of septa 248.

As discussed above, embodiments of the invention may be implemented with a mammography x-ray 3D imaging system such as mammography x-ray 3D imaging system 230. However, embodiments of the invention may also be implemented in other imaging systems that employ flat panel x-ray detectors. Since embodiments of the invention do not employ anti-scatter grids that move during imaging, manufacturing and sales costs are reduced since the cost associated with manufacturing and assembling moving components are avoided.

It is contemplated that x-ray detector assembly 232 may be readily removable from mammography x-ray 3D imaging system 230. Likewise, it is contemplated that x-ray detector unit 134 of FIG. 2 and x-ray detector unit 168 of FIG. 3 may be readily removable from any x-ray imaging system associated therewith. As such, x-ray detector units (e.g., 134, 168, 230) may be portable allowing easy transport of anti-scatter grids and x-ray detectors thereof, thus, giving clinicians or maintenance individuals greater degrees of freedom.

In accordance with one embodiment, an x-ray detector unit includes an anti-scatter grid free of at least one of a top cover and a bottom cover, a flat panel x-ray detector having an x-ray conversion layer, and an integrated anti-scatter grid assembly configured to provide structural support to the anti-scatter grid and to provide mechanical protection to the flat panel x-ray detector. The anti-scatter grid is configured to absorb a plurality of scattered x-rays impinging on the anti-scatter grid while substantially allowing un-scattered x-rays to pass through the anti-scatter grid. The x-ray conversion layer is configured to convert an x-ray into visible light or an electronic signal. The flat panel x-ray detector is fixed relative to the anti-scatter grid such that the anti-scatter grid remains stationary relative to the flat panel x-ray detector during operation of the x-ray detector.

In accordance with another embodiment, a method of manufacturing an x-ray detector unit includes forming an integrated anti-scatter grid assembly removably coupleable to an x-ray imaging system, coupling a flat panel x-ray detector to the integrated anti-scatter grid assembly, forming an anti-scatter grid having top portion and a bottom portion, and coupling the anti-scatter grid to the integrated anti-scatter grid assembly. The integrated anti-scatter grid assembly configured to support an imaging object and the anti-scatter grid is configured to absorb at least a portion of a plurality of scattered x-rays while allowing a plurality of non-scattered x-rays to pass therethrough. The anti-scatter grid is also configured to remain stationary relative to the flat panel x-ray detector during operation of the flat panel x-ray detector.

In accordance with yet another embodiment, an x-ray detector unit includes an integrated anti-scatter grid assembly, a flat panel x-ray detector coupled to the integrated anti-scatter grid assembly, and an anti-scatter grid coupled to the integrated anti-scatter grid assembly such that the anti-scatter grid remains in a substantially fixed position in relation to the flat panel x-ray detector during operation of the flat panel x-ray detector. The anti-scatter grid includes a plurality of septa having a length dimension greater than a width dimension and arranged such that the length dimension of each septum of the plurality of septa is substantially parallel to a length dimension of an adjacent septum of the plurality of septa. The anti-scatter grid is configured to allow x-rays to pass between adjacent septa of the plurality of septa. The integrated anti-scatter grid assembly is configured to support an imaging object and is configured to provide mechanical protection to the flat panel x-ray detector. The flat panel x-ray detector is configured to transmit information indicative of attenuated x-rays to a processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray detector unit comprising:
    an anti-scatter grid configured to absorb a plurality of scattered x-rays impinging on the anti-scatter grid while substantially allowing un-scattered x-rays to pass through the anti-scatter grid, wherein the anti-scatter grid is free of at least one of a top cover and a bottom cover;
    a flat panel x-ray detector comprising an x-ray conversion layer, the x-ray conversion layer configured to convert an x-ray into one of a visible light and an electronic signal, wherein the flat panel x-ray detector is fixed relative to the anti-scatter grid such that the anti-scatter grid remains stationary relative to the flat panel x-ray detector during operation of the x-ray detector;
    an integrated anti-scatter grid assembly configured to provide structural support to the anti-scatter grid and to provide mechanical protection to the flat panel x-ray detector; and
    a foam-like layer oriented above a top portion of the anti-scatter grid and within a pocket-like portion of the integrated anti-scatter grid assembly comprising a top portion and a bottom portion, wherein the top portion of the anti-scatter grid is positioned below the bottom portion of the foam-like layer and a portion of the integrated anti-scatter grid assembly separates the top portion of the anti-scatter grid from the bottom portion of the foam-like layer for increasing rigidity of the anti-scatter grid.

2. The x-ray detector unit of claim 1 wherein the anti-scatter grid is free of the top and bottom covers.

3. The x-ray detector unit of claim 1 wherein the integrated anti-scatter grid assembly is configured to support an imaging object.

4. The x-ray detector unit of claim 1 wherein the anti-scatter grid comprises:
    a plurality of septa positioned such that a gap is formed between consecutive septa of the plurality of septa and such that an edge of each septa is parallel with an edge of each consecutive septa, wherein the edges of the plurality of septa have a line frequency of greater than 200 lines per inch.

5. The x-ray detector unit of claim 4 wherein the x-ray detector unit is configured to be oriented at a first position relative to an x-ray source that is moveable along an arcuate path, and wherein a projection of the arcuate path onto the anti-scatter grid oriented at the first position is substantially parallel to the edge of each septum of the plurality of septa.

6. The x-ray detector unit of claim 1 wherein the foam-like layer comprises a material substantially transparent to x-rays.

7. The x-ray detector unit of claim 6 wherein the foam-like layer material is configured to provide structural support to the anti-scatter grid.

8. A method of manufacturing an x-ray detector unit comprising:
    forming an integrated anti-scatter grid assembly comprising a pocket like portion and removably coupleable to an x-ray imaging system, the integrated anti-scatter grid assembly configured to support an imaging object;
    coupling a flat panel x-ray detector to the integrated anti-scatter grid assembly;
    forming an anti-scatter grid having a top portion and a bottom portion, wherein the anti-scatter grid is configured to absorb at least a portion of a plurality of scattered x-rays while allowing a plurality of non-scattered x-rays to pass therethrough;
    coupling the anti-scatter grid to the integrated anti-scatter grid assembly, wherein the anti-scatter grid is configured to remain stationary relative to the flat panel x-ray detector during operation of the flat panel x-ray detector; and
    placing a foam-like material over the top portion of the anti-scatter grid and within the pocket like portion of the integrated anti-scatter grid assembly to increase rigidity of the anti-scatter grid and provide structural support to the x-ray detector assembly, wherein the foam-like material is more x-ray transparent per cubic inch than the integrated anti-scatter grid assembly.

9. The method of claim 8, wherein the anti-scatter grid is free of an anti-scatter grid cover on one of the top portion, the bottom portion, and the top and bottom portions.

10. The method of claim 8 wherein the foam-like material is substantially transparent to x-rays in the pocket to provide support to the x-ray detector assembly.

11. The method of claim 8 wherein forming the anti-scatter grid further comprises assembling a plurality of septa such that at least one edge of each septum of the plurality of septa is arranged in parallel with at least one edge of each of the other septa.

12. The method of claim 11 wherein the plurality of septa of the anti-scatter grid has a line frequency greater than 200 lines per inch.

13. An x-ray detector unit comprising:
    an integrated anti-scatter grid assembly comprising a first portion and a second portion wherein the first portion and the second portion form a pocket-like portion and the integrated anti-scatter assembly is configured to support an imaging object and configured to provide mechanical protection to a flat panel x-ray detector;
    the flat panel x-ray detector coupled to the integrated anti-scatter grid assembly and configured to transmit information indicative of attenuated x-rays to a processor;
    an anti-scatter grid coupled to the integrated anti-scatter grid assembly such that the anti-scatter grid remains in a substantially fixed position in relation to the flat panel x-ray detector during operation of the x-ray detector, the anti-scatter grid comprising:
        a plurality of septa having a length dimension greater than a width dimension and arranged such that the length dimension of each septum of the plurality of septa is substantially parallel to a length dimension of an adjacent septum of the plurality of septa, wherein the anti-scatter grid is configured to allow x-rays to pass between adjacent septa of the plurality of septa; and
    a foam-like material provided within the pocket and wherein the anti-scatter grid is positioned between the first portion of the integrated anti-scatter grid assembly and the second portion of the integrated anti-scatter grid assembly wherein the foam like material is configured to increase rigidity of the anti-scatter grid.

14. The x-ray detector unit of claim 13 wherein the foam-like material is configured to be substantially transparent to x-rays.

15. The x-ray detector unit of claim 13 wherein the integrated anti-scatter grid assembly is configured to be positioned such that a length direction of each of the plurality of septa is substantially perpendicular to an axis of rotation of an x-ray source during operation of the x-ray source and the flat panel x-ray detector.

16. The x-ray detector unit of claim 13 wherein the anti-scatter grid is free of one of a top cover, a bottom cover, and the top and bottom covers.

* * * * *